(12) United States Patent
Taylor

(10) Patent No.: US 6,599,539 B1
(45) Date of Patent: Jul. 29, 2003

(54) PERILLA SEED PESTICIDE

(75) Inventor: Thomas Dwayne Taylor, Lakeland, FL (US)

(73) Assignee: Poulenger USA Inc., Lakeland, FL (US)

(*) Notice: Subject to any disclaimer, the term of this patent is extended or adjusted under 35 U.S.C. 154(b) by 0 days.

(21) Appl. No.: 10/209,096

(22) Filed: Jul. 31, 2002

(51) Int. Cl.[7] ................................................ A61K 35/78

(52) U.S. Cl. .................... 424/725; 424/776; 424/405

(58) Field of Search ................................ 424/725, 776, 424/405

(56) References Cited

U.S. PATENT DOCUMENTS 5,658,954 A * 8/1997 Targosz
6,217,875 B1 * 4/2001 Murai et al.

* cited by examiner

*Primary Examiner*—Leon B. Lankford, Jr.
*Assistant Examiner*—Susan D Coe

(57) ABSTRACT

The invention provides a novel pesticide comprised of the seed and/or seed oils of the genus *Perilla frutescens*, commonly known as Perilla or Wild sesame, and methods for controlling plant parasitic nematodes and deterring or repelling plant damaging insects. The present invention may replace synthetically produced pesticides, such as organophosphates, which are harmful to humans and the environment, with a natural organic alternative.

3 Claims, No Drawings

PERILLA SEED PESTICIDE

BACKGROUND OF INVENTION

Pesticides are currently utilized to prevent destruction of many plants and food crops by invading insects. Many commercially available synthetically produced pesticides are being phased out, banned or restricted from use due to environmental and human health concerns. With the elimination of certain toxic pesticides, such as organophosphates, many growers and end users of these pesticides are searching for naturally occurring, environmentally safe alternatives.

One type of pest currently treated by synthetically produced chemicals is the plant parasitic nematode. These soil born pathogenic parasites can destroy roots, deplete nutrients and reduce growth of agricultural crops, turf, trees and ornamentals thus resulting in economic losses. Since the majority of the commercially available pesticides to treat for nematodes are toxic, they are banned, restricted from use or being removed from the market by the manufacturer. Practical cost effective safe alternatives are currently needed.

Some plant species contain naturally occurring compounds that can deter or repel insects and can reduce or eliminate nematode infestations upon contact. One such plant species, *Perilla frutescens* commonly known as Perilla or wild sesame, produces a seed that contains these compounds.

SUMMARY OF INVENTION

The present invention is to be utilized as a pesticide, insecticide and nematicide for the control of root damaging parasitic nematodes and other insects which can cause harm to agricultural crops, turf and ornamentals. And to be utilized as a cost effective replacement or alternative to synthetically produced pesticides that can cause harm to humans, animals, aquatic life or the environment.

The inventor has found that naturally occurring compounds which are present in the seed of the species *Perilla frutescens*, commonly known as Perilla or Wild Sesame Seed, can reduce or eliminate harmful infestations of soil born pathogenic parasitic nematodes and deter or repel other insects from feeding on the plants thus reducing economic loss.

The embodiment of the invention is the utilization of the harvested seed from the species *Perilla frutescens*, and applied to the soil or plant in various forms to be used as a pesticide.

In accordance with a further embodiment of the invention, the oil from the seed of the species *Perilla frutescens* is extracted by means of cold pressure extraction or solvent extraction and is applied to the soil or plant at varying amounts. The seed oil can either be sprayed topically by means of a suitable agriculture sprayer or can be delivered to the subsurface soil by means of a subsurface soil injector.

In accordance with a further embodiment of the invention, the seed meal which is the by product of oil extraction of the seed of the *Perilla frutescens* can be mechanically ground to varying consistencies and applied to the soil at varying amounts. The seed meal can either by topically applied in a dry form by means of a suitable spreader or can be mixed with water as a slurry and incorporated into the subsurface soil by means of a subsurface soil injector.

In accordance with a further embodiment of the invention, the whole seed of the *Perilla frutescens* plant with oils intact is mechanically ground to varying consistencies and applied to the soil at varying amounts. The whole ground seed can either by topically applied in a dry form by means of a suitable spreader or can be mixed with water as a slurry and incorporated into the subsurface soil by means of a subsurface soil injector.

DETAILED DESCRIPTION

The present invention of Perilla Seed Pesticide contains naturally occurring compounds that deter or repel damaging insects and reduce or eliminate root invading parasitic nematodes.

The seed from the plant *Perilla frutescens*, commonly know as Perilla or Wild Sesame, contains varying amounts of Linoleic acid, Alpha linoleic acid, Oleic acid and other fatty acids. These compounds, once released from the seed, can disrupt life cycles of damaging parasitic nematodes and deter or repel damaging insects from feeding upon the plant.

The Linoleics contained within the seed are drying agents which once applied to or incorporated into the soil can be consumed or absorbed by the parasitic nematode thus drying the nematode which will stop the feeding and reproductive process thus reducing or eliminating parasitic nematode populations.

The Linoleics and fatty acids contained within the seed deter or repel most leaf damaging insects due to the unpleasant taste and aroma.

The seed oil that is produced from the Perilla seed by a cold pressure extraction process or by a solvent extraction process has the highest concentration of these naturally occurring compounds. The seed oil can be applied directly to the surface of the plant in sufficient quantities to deter or repel insects by means of a suitable topical sprayer. And the Perilla seed oil can be applied to the soil by means of a suitable topical sprayer or incorporated into the soil by means of a subsurface soil injector in sufficient quantities to reduce or eliminate parasitic nematode populations.

The Perilla seed meal, which is a by-product of oil extraction, contains a significant amount of the compounds and contains beneficial organic components which amends the soil for suitable growing conditions of turf, agricultural crops and ornamentals. The seed meal is mechanically ground to varying consistencies and applied dry to the surface of the soil by means of a suitable spreading device, or can be mixed with water to form a slurry and incorporated into the subsurface soil by means of a suitable subsurface soil injector in sufficient quantities to reduce or eliminate parasitic nematode populations.

The whole ground Perilla seed with oils intact, which mechanically ground to varying consistencies, contains significant amounts of the compounds and contains beneficial organic components which amends the soil for suitable growing conditions of turf, agricultural crops and ornamentals. The whole ground seed can be applied dry to the surface of the soil by means of a suitable spreading device, or can be mixed with water to form a slurry and incorporated into the subsurface soil by means of a suitable subsurface soil injector in sufficient quantities to reduce or eliminate parasitic nematode populations.

Although the invention has been described with detail, other versions and variations are possible. Therefore the preferred embodiments of the present invention have been described, the present invention is not limited to these preferred embodiments, but includes variations and modifications within the scope and spirit of the claims.

What is claimed is:

1. A method for controlling soil born plant parasitic nematodes on plants, the plants having parts thereof extending into soil, the method comprising producing perilla seed meal as a by-product of a perilla oil cold pressure extraction process, grinding the perilla seed meal producing ground perilla seed meal, and applying the ground perilla seed meal to soil in which are growing plants having plant parasitic nematodes.

2. The method of claim 1 wherein the perilla seed meal is applied dry onto the soil by a spreading device.

3. The method of claim 1 further comprising mixing the perilla seed meal with water to form a slurry, and injecting the slurry into the soil around the plants.

* * * * *